United States Patent [19]

Carpentier et al.

[11] 4,451,936
[45] Jun. 5, 1984

[54] SUPRA-ANNULAR AORTIC VALVE

[75] Inventors: Alain Carpentier, Paris, France; Ernest Lane, Huntington Beach, Calif.

[73] Assignee: American Hospital Supply Corporation, Evanston, Ill.

[21] Appl. No.: 332,544

[22] Filed: Dec. 21, 1981

[51] Int. Cl.³ .............................................. A61F 1/22
[52] U.S. Cl. ......................................................... 3/1.5
[58] Field of Search ........................................ 3/1.5, 1

[56] References Cited

U.S. PATENT DOCUMENTS

| | | | |
|---|---|---|---|
| 3,197,788 | 8/1965 | Segger | 3/1.5 |
| 3,508,281 | 4/1970 | Cromie | 3/1.5 |
| 3,744,060 | 7/1973 | Bellhouse et al. | 3/1.5 |
| 3,755,823 | 9/1973 | Hancock | 3/1.5 |
| 4,035,849 | 7/1977 | Angell et al. | 3/1.5 |
| 4,106,129 | 8/1978 | Carpentier et al. | 3/1.5 |
| 4,343,048 | 8/1982 | Ross et al. | 3/1.5 |

Primary Examiner—Ronald L. Frinks
Attorney, Agent, or Firm—Gordon L. Peterson

[57] ABSTRACT

An aortic prosthetic valve for supra-annular implantation comprising a valve body of generally annular configuration and a valve element movably mounted on the valve body for opening and closing the valve. The valve body terminates in a generally annular base surface, and a scalloped suture ring circumscribes the valve body adjacent the base surface. The suture ring is configured to approximately fit the contour of the Sinuses of Valsalva at the base of the aorta. The base surface of the valve body is of a wavy configuration and is configured such that it does not project into the annulus at the base of the aorta, and accordingly, the valve body does not interfere with flow through the annulus. The suture ring has three lobes which fit the Sinuses of Valsalva at the base of the aorta. The valve is configured to minimize disruption of the vortices which develop in the Sinuses of Valsalva to assist in closing the valve.

10 Claims, 9 Drawing Figures

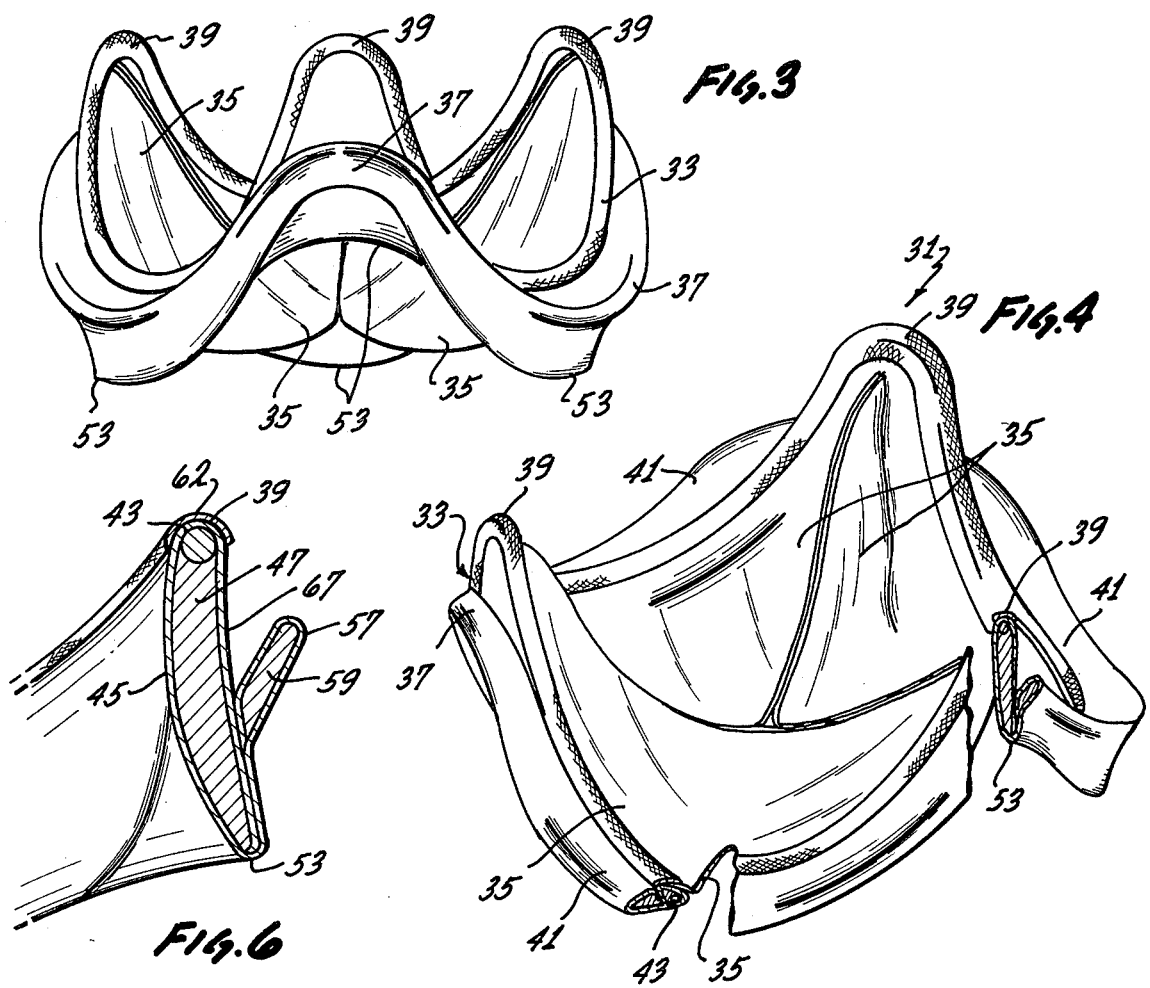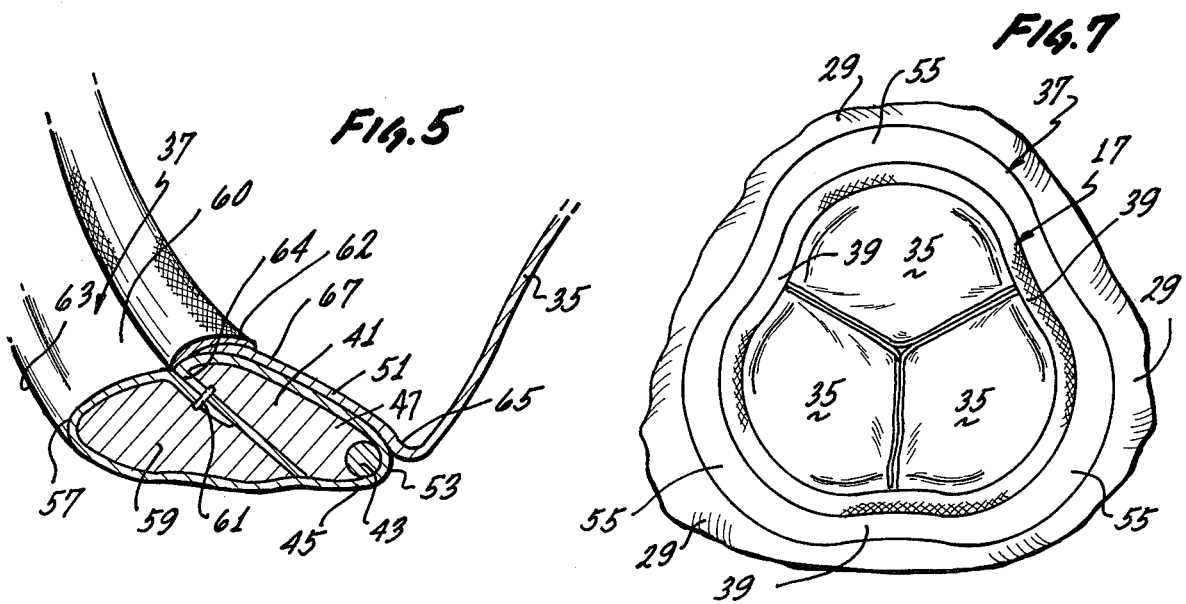

SUPRA-ANNULAR AORTIC VALVE

BACKGROUND OF THE INVENTION

A prosthetic heart value intended for replacement of a diseased natural aortic valve typically includes a valve body of generally annular configuration, a valve element movably mounted on the valve body for opening and closing the valve, and a suture ring circumscribing the valve body. In the case of a mechanical valve, the valve element may include a ball or a disc. In a leaflet type of valve, the valve element is in the form of valve leaflets.

Implantation of an aortic prosthetic heart valve of this type typically involves, among other things, suturing of the suture ring within the annulus of the aortic valve at the base of the aorta. When placed in this fashion, the valve element lies at the base of the aorta, and the valve body has an annular protrusion which extends through the annulus at the base of the aorta.

One problem created by aortic prostheses of this type is that the projection of the valve body into and through the annulus increases resistance to blood flow and reduces the hemodynamic performance of the valve. In addition, leaflet-type aortic prostheses project from the annulus in a way that disrupts the vortices which develop in the Sinuses of Valsalva. This is undesirable because these vortices assist in closing the valve.

SUMMARY OF THE INVENTION

This invention materially improves the hemodynamic performance of an aortic prosthetic valve by providing a valve which is configured for supra-annular implantation at the base of the aorta. The valve of this invention does not project into or through the annulus where it would interfere with, or restrict, the passage of blood through the annulus. In addition, the valve of this invention is configured so as to minimize disruption of the vortices which develop in the Sinuses of Valsalva. This is particularly important in leaflet-type valves.

Although this invention is applicable to mechanical heart valves and leaflet-type heart valves, it provides additional advantages for leaflet-type valves. For example, because the stent does not project into the annulus, a larger leaflet-type valve may be utilized for an annulus of given size. This is of particular advantage in the smaller size heart valves where mechanical aortic prostheses have heretofore demonstrated superior hemodynamic performance when compared to certain leaflet-type valves of equivalent annulus or mounting diameter.

In a leaflet-type valve constructed in accordance with this invention, the stent is preferably completely out of the annulus. Only the leaflets of the valve remain exposed to the blood column.

The aortic valve of this invention has several structural features which adapt it for supra-annular implantation. For example, the suture ring which circumscribes the valve body is scalloped more than is customary for an aortic prosthetic valve so as to adapt it even more to the scalloped configuration of the sinus cavities at the base of the aorta. Thus, the suture ring is scalloped and configured to approximately fit the contour of the Sinuses of Valsalva at the base of the aorta. Preferably, the suture ring has three lobes as viewed in plan so that it more closely conforms to the configuration of the sinus cavities at the base of the aorta.

The valve body on which the valve element is movably mounted, terminates in a generally annular base surface adjacent the suture ring. The base surface is of a wavy configuration and configured so that it does not project into the annulus at the base of the aorta when the suture ring is in place in the Sinuses of Valsalva. By way of contrast, the typical leaflet-type aortic valve has an annular projection below the suture ring which projects through an annulus. Similarly, the valve body of the typical mechanical aortic heart valve is sized so as to be implanted within the annulus. Accordingly, by configuring the base surface so that it does not project into the annulus, only the valve element lies in the flow path through the annulus.

In a leaflet-type valve of this invention, the valve body includes generally axially extending commissure supports which terminate in free ends and intercommissural regions which space the commissure supports circumferentially. In addition, the valve element includes valve leaflets on the valve body, and the wavy base surface is remote from the free ends of the commissure supports. In a leaflet-type valve, the lobes on the suture ring project radially outwardly at the intercommissural regions.

To minimize disruption of the vortices which develop to assist in valve closure, this invention substantially reduces or eliminates the axial projection heretofore typically found on leaflet-type aortic prosthetic valves. Thus, with this invention, the valve has a surface at the intercommissural regions which extends between the inner periphery of the suture ring and the outer periphery of the valve leaflets on the side of the suture ring remote from the annulus when the suture ring is in place in the Sinuses of Valsalva. This surface is configured to minimize disruption of the vortices. Thus, this surface does not contain the characteristic axial projection of the prior art. Rather, this surface is flared as it extends from the inner periphery of the valve leaflets to the outer periphery of the valve body. Although optimum performance is obtained when all of the features of this invention are used in combination, these features can be used individually or in various subcombinations, if desired.

The invention, together with additional features and advantages thereof, may best be understood by reference to the following description taken in connection with the accompanying illustrative drawings.

BRIEF DESCRIPTION OF THE DRAWING

FIG. 3 is an elevational view of the valve.

FIG. 4 is a perspective view of the valve with parts broken away to show the configuration of the valve at one of the commissure supports and one of the intercommissural regions.

FIG. 5 is an enlarged fragmentary sectional view in partially schematic form taken on a radial plane at one of the intercommissural regions.

FIG. 6 is an enlarged fragmentary sectional view in partially schematic form taken on a radial plane at the top of one of the commissure supports.

FIG. 7 is a top plan view of the valve implanted in a supra-annular position.

DESCRIPTION OF THE PREFERRED EMBODIMENT

Figure 1:
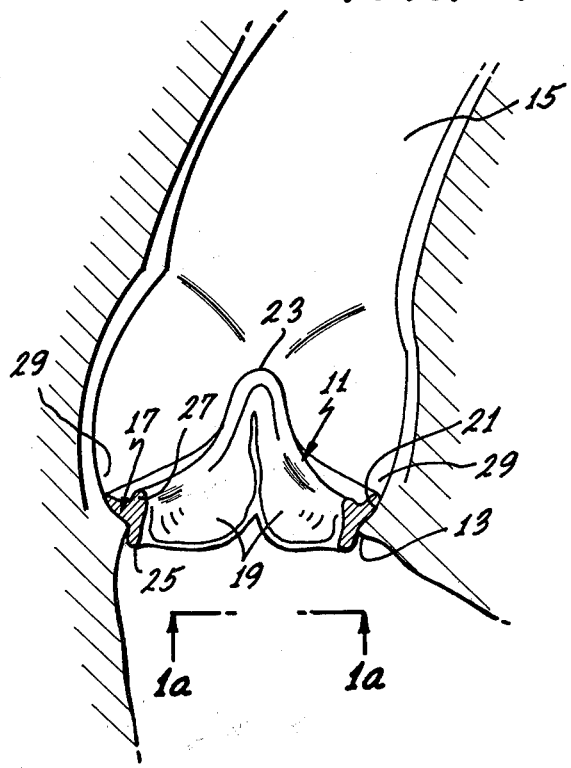
FIG. 1 is a fragmentary sectional view through a human heart at the base of the aorta with a prior art aortic valve implanted therein.
Figure 1A:
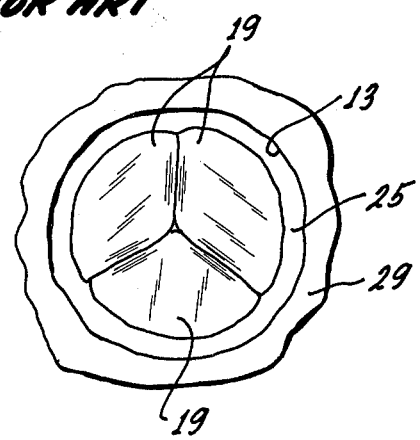
FIG. 1a is a bottom plan view of the prior art valve of FIG. 1.

FIGS. 1 and 1a show a typical prior art aortic prosthetic heart valve 11 implanted within an aortic annulus 13 at the base of the aorta 15. By way of example, the valve 11 may be of the type shown in French Patent Application No. 7834510 (Publication No. 2,433,933), Angell et al U.S. Pat. No. 3,983,581 or Carpentier et al U.S. Pat. No. 4,106,129.

The heart valve 11 includes an annular valve body 17, three valve leaflets 19 mounted on the valve body and a suture ring 21 surrounding the valve body and projecting radially outwardly of the valve body. The valve body includes three commissure supports 23, and the suture ring 21 is slightly scalloped. The valve body 17 has an annular segment 25 which projects axially below the suture ring 21 and a generally annular segment 27 which projects generally axially above the suture ring.

The prior art valve 11 is implanted within the annulus 13 at the base of the aorta. When implanted in this manner, the annular segment 25 extends through the annulus 13, and the annular segment 27 projects above the suture ring 21 between the outer periphery the suture ring 21 and the outer periphery of the valve leaflets 19 as shown in FIG. 1. As shown in FIGS. 1 and 1a, the annular segment 25 restricts the area of the annulus and interferes with the flow of blood through the annulus. A mechanical heart valve is typically implanted into the annulus 13 and also reduces the cross-sectional area of the flow passage at the annulus. In addition, the annular segment 27 has been found to disrupt the vortices which are formed in sinus cavities 29 and which assist in closing the valve leaflets 19.

FIGS. 2-7 show an aortic heart valve 31 constructed in accordance with the teachings of this invention. The valve 31 includes a resilient annular valve body 33, a valve element in the form of three valve leaflets 35 movably mounted on the valve body for opening and closing the valve, and a scalloped suture ring 37 circumscribing the valve body. The valve body includes three generally axially extending commissure supports 39 and three intercommissural regions 41 which space the commissure supports circumferentially.

In the embodiment illustrated, the valve body and suture ring have a novel external configuration. However, this invention is not limited by the manner in which this external configuration is obtained, and accordingly, the specific internal construction of the valve body is not described in detail herein. The internal construction and the technique for constructing an aortic heart valve body and suture ring are well known, and by way of example, the valve body 33 and suture ring 37, except for having a different configuration, may be constructed generally in accordance with Carpentier, et al., U.S. Pat. No. 4,106,129 which also provides a valve body having the desired resilience.

Generally, the valve body 33 includes a frame 43 of wire or other suitable material, a fabric cover 45 and other conventional components, such as cloth coverings, plastic linings, etc. within the cover, and for simplicity, these components are designated herein as filler elements 47, and also for simplicity, are shown schematically in FIGS. 4-6. The valve leaflets 35 may be tissue or synthetic material. In the drawings, a porcine valve is illustrated, and the leaflets 35 are integrally joined to an aortic segment 51. The aortic segment 51 may be sutured to the fabric cover 45 of the valve body in a conventional manner.

The valve body 17 has a base surface 53 which is of wavy configuration (FIGS. 3 and 4) and configured such that it does not project into the annulus 13 at the base of the aorta 15 when the suture ring 37 is in place in the sinus cavities 29. The base surface 53 smoothly curves from a low position at the center of each of the intercommissural regions 41 to an uppermost location which is axially aligned with the centers of the commissure supports 39.

The suture ring 37 is also of wavy or scalloped configuration, with the high points of the waves being axially aligned with the centers of the commissure supports 35, respectively, and with the low points of the waves occurring at the central regions of the intercommissural regions 41, respectively. Thus, the undulations or waves of the suture ring 37 are in phase with the undulations of the base surface 53.

The suture ring 37 has three lobes 55 (FIG. 7) which are configured to fit the corresponding cavities 29. Except for the lobes 55 and the exaggerated wavy configuration, the suture ring 37 may be of conventional construction. Thus, the suture ring 37 may include a fabric cover 57 enclosing a compliant annular filler 59 of any suitable material or materials commonly used for this purpose. In the embodiment illustrated, the cover 57 is formed by an extension of one end of the fabric cover 45, and sutures 61 may be used to suitably join the layers of the fabric together as shown in FIG. 5. An optional, annular fabric strip 62 (FIGS. 5 and 6) covers the outer periphery of the aortic segment 51 and the adjacent region of the fabric cover 45 and is suitably attached to the cover 45.

The valve 31 has an outer periphery 63 (FIG. 5) which is defined by the outer periphery of the suture ring 37. The suture ring 37 has an inner periphery 64 and a surface 60 which, as viewed in axial cross section, is generally transverse to the axis of the valve. The valve leaflets 35 have what may be considered an outer periphery 65 where the leaflets 35 meet the valve body 33 and the aortic segment 51. The valve 31 has a surface 67 at the intercommissural regions 41 (FIG. 5) which extends between the peripheries 64 and 65 on the upper side of the valve. In the embodiment illustrated, the the surface 67 is defined by a surface of the aortic segment 51 and a surface of the fabric strip 62. The surface 67 is flared as it extends between the peripheries 64 and 65. Specifically, the surface 67 extends axially upwardly and radially outwardly and is devoid of prominent axial projections, although the strip 62, when used, may create a modest projection. For example, the surface 67 may be inclined at an angle of 20 degrees or more from the axis of the valve. Thus, the surface 67 is configured to minimize disruption of the vortices which develop in the sinus cavities 29 to assist in closing the valve leaflets 35. Although the surface 67 also exists at the commissure supports 39, as shown in FIG. 6, the surface 67 has a different configuration at the top of the commissure supports. However, it is the configuring of the surface 67 at intercommissural regions 41 which minimizes disruption of the vortices, and the configuration of the surface 67 at the commissure supports is of no particular significance with respect to vortex disruption.

Figure 2:
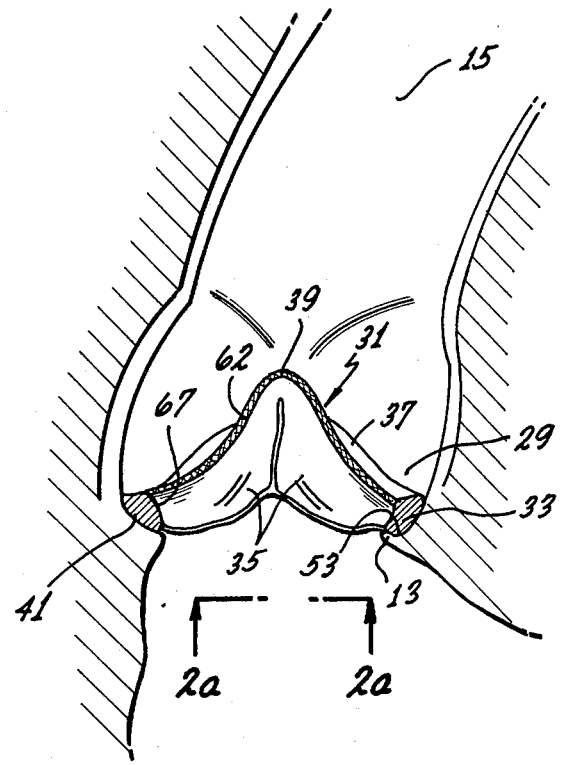
FIG. 2 is a sectional view similar to FIG. 1 with a valve constructed in accordance with the teachings of this invention implanted in a supra-annular position.
Figure 2A:
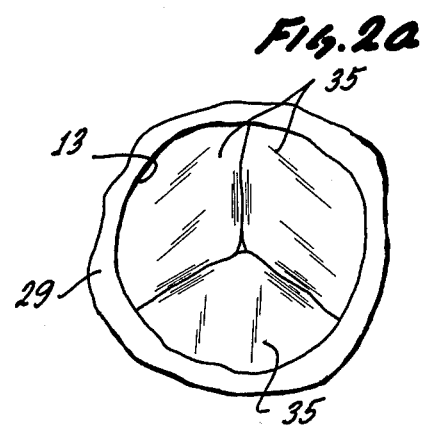
FIG. 2a is a bottom plan view of the construction shown in FIG. 2.

The valve 31 may be implanted in a supra-annular position as shown in FIGS. 2 and 2a. For example, the aorta 15 may be opened transversely above the sinus cavities 29 and the diseased natural valve is removed. The valve 31 is deformed radially and inserted through the aortic segment into the sinus cavities 29 where it is allowed to resiliently return to its essentially undeformed condition. The suture ring 37 is sutured to the base of the sinus cavities 29, and the valve body 33 is completely out of the annulus 13 so that only the valve leaflets 35 are in the flow path through the annulus. This is made possible by the base surface 53 being of the wavy configuration illustrated and configured such that it does not project into the annulus 13. Also, the valve 31 is of a larger size than would ordinarily be used for the size of the annulus 13.

The suture ring 37 is placed into the sinus cavities 29 such that its wavy configuration fits or matches the configuration of the cavities 29 and also so that the lobes 55 are received within the complementary cavities 29. As shown in FIG. 2, the flared surface 67 at each of the intercommissural regions 41 contains no axial projection which would disrupt the vortices formed in the cavities 29. Accordingly, valve closure is improved with the supra-annular mounting of the valve 31.

Although an exemplary embodiment of the invention has been shown and described, many changes, modifications and substitutions may be made by one have ordinary skill in the art without necessarily departing from the spirit and scope of this invention.

We claim:

1. An aortic prosthetic valve for supra-annular implantation comprising:
    a valve body of generally annular configuration and a valve element movably mounted on the valve body for opening and closing the valve, said valve body terminating in a generally annular base surface;
    a scalloped suture ring circumscribing said valve body adjacent said base surface and configured to approximately fit the contour of the Sinuses of Valsalva at the base of the aorta; and
    said base surface of said valve body being of a wavy configuration and configured such that it does not project into the annulus at the base of the aorta when the suture ring is in place in the Sinuses of Valsalva whereby the aortic prosthetic valve can be mounted in a supra-annular position and the valve body does not interfere with flow through the annulus.

2. A valve as defined in claim 1 wherein said suture ring as viewed in plan has three lobes.

3. A valve as defined in claim 1 wherein said valve body includes generally axially extending commissure supports which terminate in free ends and intercommissural regions which space the commissure supports circumferentially, said valve element includes valve leaflets on the valve body, said base surface being remote from the free end of the commissure supports.

4. A valve as defined in claim 3 wherein said suture ring has a radially outwardly projecting lobe between each adjacent pair of commissure supports.

5. A valve as defined in claim 4 wherein the valve has a surface at the intercommissural regions which extends between the inner periphery of the suture ring and the outer periphery of the valve leaflets on the side of the suture ring remote from the annulus when the suture ring is in place in the Sinuses of Valsalva, said surface being flared as it extends between said outer peripheries.

6. A valve as defined in claim 3 wherein the valve has a surface at the intercommissural regions which extends between the inner periphery of the suture ring and the outer periphery of the valve leaflets on the side of the suture ring remote from the annulus when the suture ring is in place in the Sinuses of Valsalva, said surface being configured to minimize disruption of the vortices which develop in the Sinuses of Valsalva to assist in closing the valve leaflets.

7. A valve as defined in claim 1 wherein said valve is devoid of an annular projection below the suture ring when the suture ring is in place in the Sinuses of Valsalva.

8. A valve as defined in claim 3 wherein the valve is constructed so that only the valve leaflets are in the flow path through the annulus.

9. A valve as defined in claim 6 wherein said suture ring has a radially outwardly projecting lobe between each adjacent pair of commissure supports, said valve is devoid of an annular projection below the suture ring when the suture ring is in place in the Sinuses of Valsalva, and said valve is constructed so that only the valve leaflets are in the flow path through the annulus.

10. A method comprising:
    providing an aortic prosthetic valve which includes a valve body of generally annular configuration, a valve element movably mounted on the valve body for opening and closing the valve, and a scalloped suture ring circumscribing the valve body and configured to approximately fit the contour of the Sinuses of Valsalva at the base of the aorta, said valve body terminating in a generally annular base surface of a wavy configuration; and
    implanting said aortic prosthetic valve in a human heart with the suture ring being received in the Sinuses of Valsalva at the base of the aorta and with the base surface of the valve body being out of the annulus at the base of the aorta so that the valve body does not interfere with flow through the annulus.

* * * * *